United States Patent
Goble et al.

(10) Patent No.: US 6,893,414 B2
(45) Date of Patent: May 17, 2005

(54) INTEGRATED INFUSION AND ASPIRATION SYSTEM AND METHOD

(75) Inventors: E. Marlowe Goble, Logan, UT (US); Mark E. Howard, San Diego, CA (US); Jeffrey T. Mason, Escondido, CA (US); T. Wade Fallin, Hyde Park, UT (US)

(73) Assignee: Breg, Inc., Vista, CA (US)

( * ) Notice: Subject to any disclaimer, the term of this patent is extended or adjusted under 35 U.S.C. 154(b) by 264 days.

(21) Appl. No.: 10/218,106

(22) Filed: Aug. 12, 2002

(65) Prior Publication Data

US 2004/0030281 A1 Feb. 12, 2004

(51) Int. Cl.⁷ .............................................. A61M 1/00
(52) U.S. Cl. ............................ 604/27; 604/43; 604/40
(58) Field of Search ........................ 604/27–30, 35–38, 604/43, 120

(56) References Cited

U.S. PATENT DOCUMENTS

| | | | |
|---|---|---|---|
| 3,771,527 A | * 11/1973 | Ruisi | ............................ 604/43 |
| 3,885,567 A | * 5/1975 | Ross | ........................... 604/120 |
| 4,619,643 A | 10/1986 | Bai | |
| 4,692,141 A | 9/1987 | Mahurkar | |
| 5,002,528 A | 3/1991 | Palestrant | |
| 5,447,494 A | * 9/1995 | Dorsey, III | .................. 604/43 |
| 5,616,121 A | 4/1997 | McKay | |
| 5,718,692 A | 2/1998 | Schon et al. | |
| 5,817,052 A | 10/1998 | Johnson et al. | |
| 5,957,879 A | * 9/1999 | Roberts et al. | ............ 604/6.06 |
| 6,001,079 A | 12/1999 | Pourchez | |
| 6,132,415 A | 10/2000 | Finch et al. | |
| 6,325,788 B1 | 12/2001 | McKay | |
| 6,340,355 B1 | * 1/2002 | Barrett | ........................ 604/27 |
| 6,409,699 B1 | * 6/2002 | Ash | ............................. 604/29 |
| 6,749,580 B2 | * 6/2004 | Gloukhoff et al. | ............ 604/29 |
| 6,758,836 B2 | * 7/2004 | Zawacki | ..................... 604/284 |

* cited by examiner

Primary Examiner—Sharon Kennedy
(74) Attorney, Agent, or Firm—Workman Nydegger (57) ABSTRACT

An integrated infusion and aspiration system includes of a flow control system and a catheter assembly. The catheter assembly includes an infusion catheter and an aspiration catheter, each having ports located at the distal end of thereof. The distal ends of the catheters are separated so that the aspiration catheter ports can be positioned on an opposing side of a surgical wound site from the infusion catheter ports. Methods of operation of the integrated infusion and aspiration system provides for uninterrupted aspiration with concurrent controlled delivery of an infusion solution such that the infusion solution is substantially evenly dispersed of over the wound site.

34 Claims, 7 Drawing Sheets

INTEGRATED INFUSION AND ASPIRATION SYSTEM AND METHOD

CROSS-REFERENCE TO RELATED APPLICATIONS

Not applicable.

BACKGROUND OF THE INVENTION

1. The Field of the Invention

The present invention relates generally to the post-surgical treatment of closed wounds and specifically to methods and systems for concurrent aspiration and infusion of a wound site to manage pain, swelling, bleeding and infection.

2. The Relevant Technology

One of the most difficult aspects of enduring a major surgical procedure is coping with the post-operative pain and swelling. Commonly, opioid analgesics, sometimes referred to as narcotics, are administered post-operatively to counter the pain associated with wound healing and recovery. However, the use of systemic opioid analgesics, whether administered by oral, intramuscular, or intravenous methods, includes a host of possible undesirable side effects, including: respiratory depression, renal function depression, nausea, constipation, ataxia, confusion, sweating, and itching. The length of hospital stay for patients undergoing a major surgical procedure is, in part, determined by the need to monitor and control the side effects of systemically administered opioid analgesics.

More recently, infusion pumps have been used to percutaneously deliver local anesthetics directly to the surgical wound. Thus, many of the undesirable side effects of systemic opioid analgesics are avoided. Furthermore, medication dosage is considerably less than systemic delivery since the medication is delivered directly to the affected site. However, contemporary percutaneous pain medication infusion pumps do not provide consistent relief of pain.

Another challenge associated with percutaneous pain medication infusion pumps is the need to concurrently address edema, or fluid build-up and swelling, at the wound site. Aspiration of excess fluid has been attempted by the use of a separate and discrete percutaneous catheter connected to a vacuum source. However, concurrent use of a pain medication infusion pump and an aspiration catheter creates two significant compromises to the patient. First, two percutaneous catheters, one for the aspiration catheter and one for the infusion pump, potentially doubles the risk of infection since two percutaneous tracts are maintained. Second, an aspiration catheter coupled with an active vacuum source that is designed for the removal of fluid build-up tends to remove the infused pain medication before it has effectively produced the desired local anesthetic effect.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
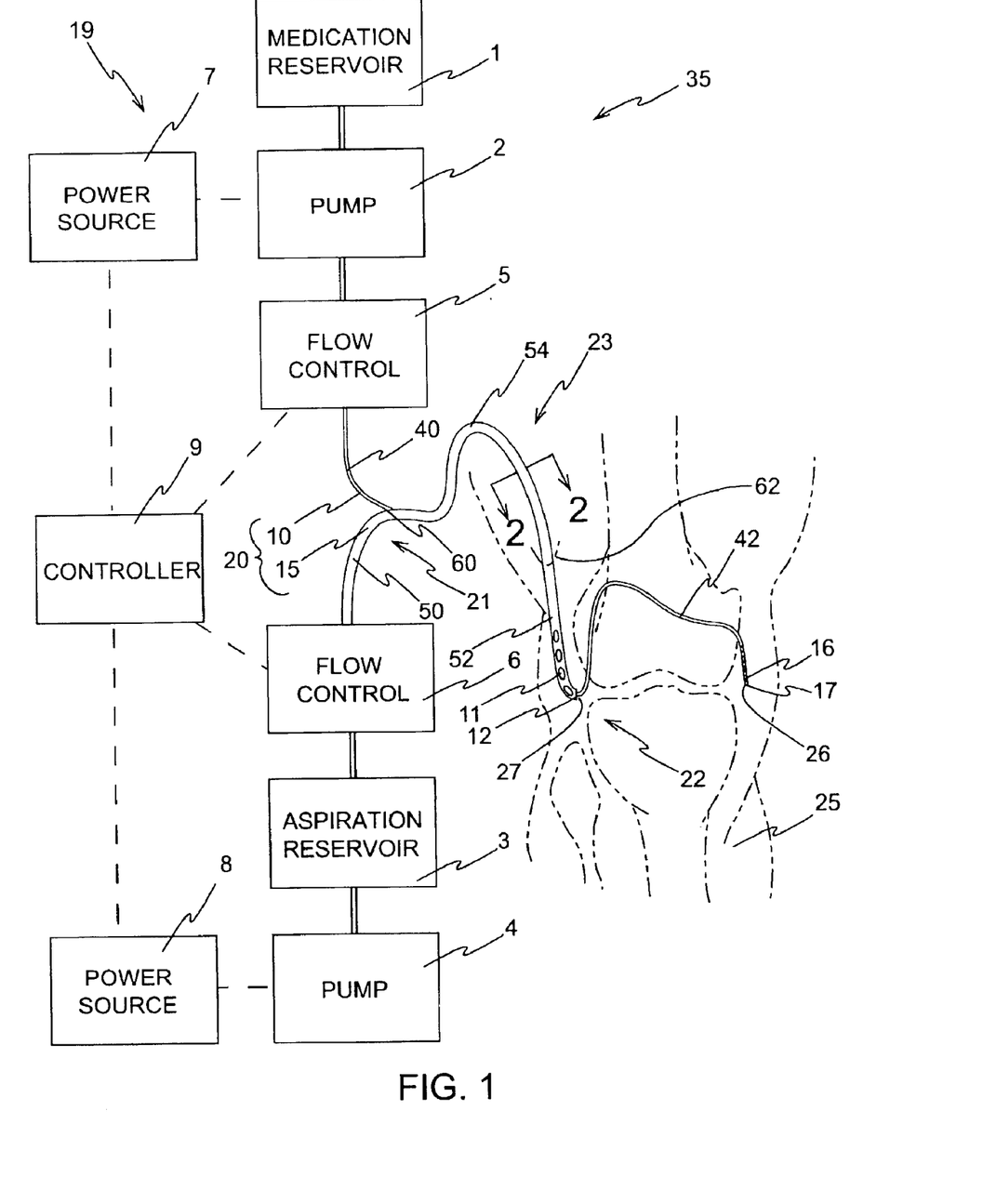
FIG. 1 is a schematic view of an integrated infusion and aspiration system applied to the knee of a patient.

Shown in FIG. 1 is one embodiment of an integrated infusion and aspiration system 35 incorporating features of the present invention. System 35 is applied to a knee 25 of a patient to treat a surgical wound that would result from, for example, a total knee arthroplasty surgery. While FIG. 1 demonstrates use of one embodiment of integrated infusion and aspiration system 35 for a knee, it is understood that the present invention can be used for any internal body wound created by surgery, trauma, or disease.

In general, integrated infusion and aspiration system 35 comprises a catheter assembly 20 coupled with a flow control system 19. Viewed as a whole, catheter assembly 20 has a proximal section 21, an opposing distal section 22, and a middle section 23 extending therebetween. More specifically, catheter assembly 20 comprises an infusion catheter 10 and an aspiration catheter 15. Infusion catheter 10 comprises a proximal section 40, an opposing distal section 42, and a middle section 44 (see FIG. 2) extending therebetween. Distal section 42 terminates at a distal end tip 17. Infusion catheter 10 bounds a first lumen 46 (FIG. 2) that extends along the length thereof and exits through an end port 26 at distal end tip 17. A plurality of longitudinally spaced apart side ports 16 extend through infusion catheter 10 at distal section 42 so as to communicate with first lumen 46. In alternative embodiments, the plurality of side ports 16 can be eliminated or replaced with one or more side ports. Furthermore, side ports 16 can be spaced laterally and/or radially.

Aspiration catheter 15 comprises a proximal section 50, an opposing distal section 52, and a middle section 54 extending therebetween. Distal section 52 terminates at a distal end tip 12. Aspiration catheter 15 bounds a second lumen 56 (FIG. 2) that extends along the length thereof and exits through an end port 27 at distal end tip 12. A plurality of spaced apart side ports 11 extend through aspiration catheter 15 at distal section 52 so as to communicate with second lumen 56. As with infusion catheter 10, the plurality of side ports 11 can be eliminated or replaced with one or more side ports 11. Furthermore, side ports 11 can be spaced laterally and/or radially.

In one embodiment, the plurality of ports of infusion catheter 10 and aspiration catheter 15 each have a predetermined number and a predetermined spacing, the number and spacing of the plurality of ports on infusion catheter 10 being substantially the same as the number and spacing of the plurality of ports on aspiration catheter 15. In other embodiments, the number and/or spacing of the ports on the infusion catheter 10 and aspiration catheter 15 can be different.

Figure 2:
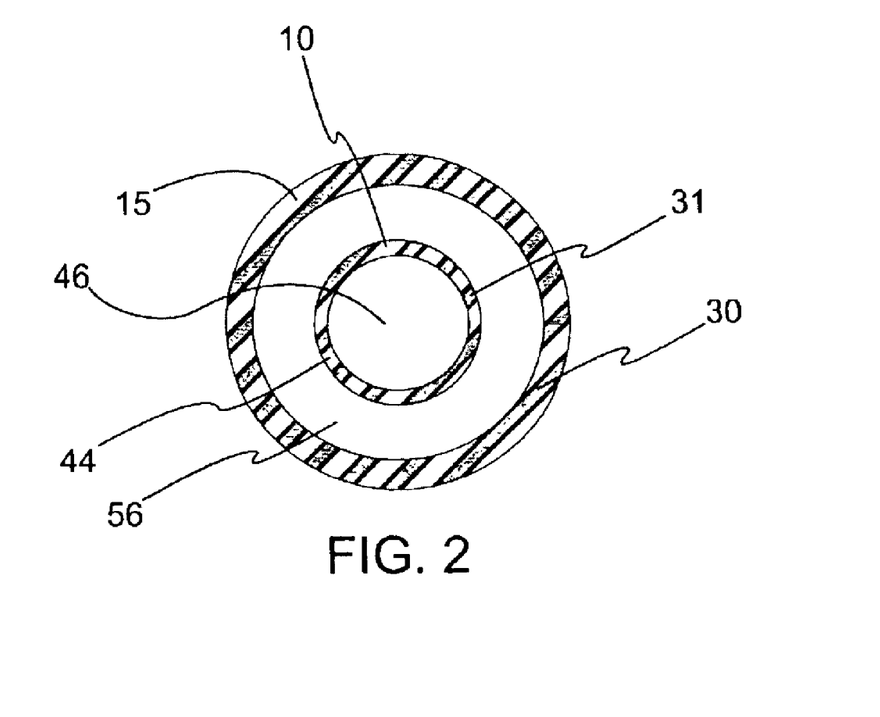
FIG. 2 is a cross sectional side view of the catheter assembly shown in FIG. 1 taken along sections lines 2—2.

In the embodiment of catheter assembly 20 shown in FIG. 1, infusion catheter 10 passes through a sidewall of aspiration catheter 15 and into second lumen 56 at a proximal junction 60. This is typically accomplished by forming a hole in the sidewall of aspiration catheter 15 and then passing infusion catheter 10 therethrough. Once infusion catheter 10 is positioned, infusion catheter 10 and aspiration catheter 15 are sealed together at the hole such as by welding, adhesive, or other conventional Infusion catheter 10 travels distally within second lumen 56 and exits aspiration catheter 15 through end port 27 at distal end tip 12. Thus, as shown in FIG. 2, infusion catheter 10 occupies an internal, coaxial position with respect to aspiration catheter 15 between proximal junction 60 and distal end tip 12 of aspiration catheter 15.

It is noted that the outer diameter of infusion catheter 10 is smaller than the inner diameter of aspiration catheter 15 so that fluid is free to flow within second lumen 56 of aspiration catheter 15. Furthermore, this arrangement provides the advantage of protecting infusion catheter 10 from possible kinking or pinching when is it positioned internal to the more substantially larger sized aspiration catheter 15. Another advantage of this arrangement is that by positioning infusion catheter 10 within aspiration catheter 15, only a single tract through the skin is required to pass both catheters 10 and 15 from an extracorporeal site to the internal wound site.

Continuing with the embodiment of catheter assembly 20 shown in FIG. 1, infusion catheter 10 extends distally from the distal end tip 12 of aspiration catheter 15 a predetermined distance so that distal end tips 12 and 17 are spaced apart. The spaced distance is sufficient so that ports 16 and 26 of infusion catheter 10 and ports 11 and 27 of aspiration catheter 15 can be positioned on opposing sides of a wound. The spacing between ports 11, 27 and 16, 26 is dependent upon wound size, but in one embodiment is more than ten times the largest external transverse dimension of aspiration catheter 15.

As shown in FIG. 1, flow control system 19 comprises a flow control 5, a pump 2, and medication reservoir 1 each operably coupled with proximal section 40 of infusion catheter 10. Similarly, a flow control 6, pump 4, and aspiration reservoir 3 are operably coupled with proximal section 50 of aspiration catheter 15. Reservoirs 1 and 3 can comprise a flexible bag, such as an IV bag, a syringe barrel, or any other conventional hard of soft sided container adapted to hold a fluid.

The infusion solution used by the present invention can contain a number of different medications to best address the post surgical concerns of the wound. For example, the infusion solution can contain, separately or in combination, an analgesic agent, an anesthetic agent, an antibiotic, an antiseptic, an anticoagulant, or an anti-inflammatory. Thus, in addition to pain relief provided by analgesic and anesthetic agents, concurrent prophylactic treatment for infection and treatment to reduce swelling can be achieved by including an antibiotic and anti-inflammatory in the infusion solution.

Pumps 2 and 4 can be any standard pump known by those skilled in the art, such as a squeeze bulb, syringe, syringe pump, syringe plunger, centrifugal pump, persistaltic pump, diaphragm pump, screw pump, IV pump, or the like. The flow controls 5 and 6 can be any standard flow control device known to those skilled in the art, such as an orifice, capillary tube, or valve. Valves include solenoid valves, servo valves, and flow restricting valves, such as a needle valve, gate valve, pinch valve, and the like. Connected to pump 2 is a power source 7, and connected to pump 4 is a power source 8. Power sources 7 and 8 can be selected from a number of power sources known by those skilled in the art, including manual actuation, spring, dc motor, ac motor, and the like.

When the power sources 7 and 8 and flow controls 5 and 6 are passive devices, such as a spring or orifice, a separate controller is not required. However, when the power sources 7 and 8 and/or flow controls 5 and 6 are not passive, a controller 9 is connected thereto. Controller 9 is generally electronic, and preferably controller 9 is a microprocessor based control device.

In one embodiment, reservoirs 1 and 3, pumps 2 and 4, flow controls 5 and 6, powers sources 7 and 8 and controller 9 collectively comprise flow control system 19. Although FIG. 1 shows the various elements of flow control system 19 in a defined order, it is appreciated that the various elements can be reorganized in a variety of different orientations using different combination of parts. For example, one configuration for flow control system 19 comprises the following selections: flow control 5 is a solenoid valve, medication reservoir 1 is a syringe barrel, pump 2 is a syringe plunger, and power source 7 is a spring which is disposed between the syringe plunger and the syringe barrel.

In this configuration, the syringe plunger is initially drawn back relative to the syringe barrel so as to fill the syringe barrel with a desired solution. In so doing, the resilient spring is stretched so that there is a constant force attempting to drive the syringe plunger back into the syringe barrel and, in turn, discharge the solution therefrom. The syringe barrel is connected in fluid communication with the proximal section of infusion catheter 10. Accordingly, the solution is passed from the syringe barrel, through infusion catheter 10, and out through ports 16, 26. The solenoid valve is disposed so as to selectively control the flow of solution from the syringe barrel into the infusion catheter.

Continuing with the example, flow control 6 is an adjustable flow restricting valve, such as a pinch valve, aspiration reservoir 3 is a syringe barrel, pump 4 is a syringe plunger, and power source 8 is a spring positioned between the syringe barrel and the syringe plunger. In this embodiment, the spring is compressed as the syringe plunger is pressed into the syringe barrel. The syringe barrel is in fluid communication with the proximal section of aspiration catheter 15. In this configuration, the spring produces a constant force seeking to push the syringe plunger out of the syringe barrel. As the syringe plunger is pushed out of the syringe barrel by the spring, a relative vacuum is produced which causes fluid to be sucked into aspiration catheter 15 through ports 11, 27 and into the syringe barrel.

Controller 9 is connected to the flow control 5 and the flow control 6, but not to power sources 7 and 8 since they are passive devices. Controller 9 is a microprocessor with embedded firmware that selectively opens and closes the flow control 5, the solenoid valve, and also increases or decreases the flow rate through partial actuation of flow control 6, the pinch valve.

An alternative configuration for flow control system 19 is comprised of the same selections as above, except that flow control 5 is an orifice that creates a flow rate proportional to the fluid pressure. Furthermore, the controller 9 is only connected to flow control 6, since flow control 5 is, in this instance, a passive device. With this configuration, a relatively constant flow rate of the infusion solution is achieved while the aspiration flow rate can be increased or decreased based the amount and time of accumulation of the infusion solution at the wound site.

As discussed above, during operation catheter assembly 20 is inserted through a single incisions 62 in the skin so that at least a portion of ports 11, 27 and 16, 26 are positioned on opposing sides of an internal wound site. In one embodiment, the ports 11, 27 and 16, 26 and corresponding catheters are disposed outside of a blood vessel. Catheter assembly 20 is coupled with flow control system 19. In one method of operation, fluid control system 19 administers at set periodic intervals a dose of infusion solution to infusion catheter 10. The dose of infusion solution passes through infusion catheter 10 and out through ports 16, 26 to one side of the wound site.

Simultaneously with the infusion of the dose, and for a predetermined time period thereafter, flow control system 19 draws fluid on the opposite side of the wound site into aspiration catheter 15 by way of ports 11, 27 at a first flow rate. Ports 16, 26 and ports 11, 27 are positioned so that aspiration of fluid by aspiration catheter 15 causes the infused dose to uniformly travel over the wound site. At the conclusion of the predetermined time period following the infusion, fluid is drawn into aspiration catheter 15 at a second flow rate, the second flow rate being faster than the first flow rate. When the next dose of infusion solution is administered, the flow rate in aspiration catheter 15 is again lowered to the first flow rate and the process is repeated.

Although not required, in one method of operation the flow in aspiration catheter 15 is never interrupted, i.e., is continuous, throughout the repeated periodic infusion of the infusion solution. This is because a standing fluid column of blood and other body fluids is likely to coagulate, thereby clogging the aspiration catheter 15.

By way of example of the operation process, in the case of the administration of a local anesthetic, such as lidocaine, bupivacaine, or ropivicaine, the dose is between about 0.5 cc and about 4 cc. The set periodic interval between administration of the doses is approximately one hour. The first flow rate at which fluid is drawn into aspiration catheter 15 during administration of the dose and the predetermined time period thereafter is between about 10% to about 30% of the dose per hour. The predetermined time period at which the aspiration catheter 15 operates at the first flow rate following infusion is equal to or longer than the time required for the medications in the infusion solution to effectively treat the wound. As such, the length of the predetermined time period is typically between about 5 minutes to about 15 minutes. Following the predetermined time period but prior to administration of the next dose, the flow rate in the aspiration catheter is controlled at a rate generally between about 4 cc/hr and about 50 cc/hr, and preferably between about 10 cc/hr and about 30 cc/hr.

The above method of operation provides a resident time for the infusion solution that allows the infusion solution to effectively treat the wound, and thereafter the infusion solution along with other accumulated body fluids are rapidly evacuated from the wound site to reduce swelling and to ameliorate associated pain.

In an alternative method of operation, each dose is delivered over an extended period of time such that aspiration catheter 10 aspirates at the first flow rate during infusion of a discrete dose and then immediately aspirates at the second flow rate upon completion of infusing that dose. As such, there is no delay, i.e, "predetermined time period," between completion of the infusion and changing the aspiration to the second flow rate. This alternative method of operation is an advantage where low pressure injections are necessary to prevent disruption of delicate internal structures that are starting to heal. Although less efficient in some situations, it is also appreciated that aspiration can be changed to the increased second flow rate prior to completion of infusion of a discrete dose.

In yet another alternate method of operation, the infusion solution is delivered at a relatively constant flow rate. In the case of the administration of a local anesthetic, such as lidocaine, bupivacaine, or ropivicaine, the flow rate of the infusion solution is preferably between about 0.5 cc/hr and about 4.0 cc/hr. The flow rate within aspiration catheter 15 is cycled between a low flow rate, generally at a rate between 10% and 30% of the infusion solution flow rate, and a high flow rate, generally between 4 cc/hr and 50 cc/hr, and preferably between 10 cc/hr and 30 cc/hr. The cycle for the low flow rate generally endures for 15 to 30 minutes, and the low flow rate cycle generally repeats approximately every 60 minutes. Thus, this alternate method of operation provides for a period time when the flow rate within infusion catheter 10 is higher than the flow rate within aspiration catheter 15, thus creating an accumulation of the infusion solution so that it may effectively treat the wound.

As previously, mentioned, contemporary percutaneous pain medication infusion pumps do not provide consistent relief of pain. It is theorized that this is because the medication that egresses from the percutaneous catheter is not fully bathing the entire volume of the wound site. Many of these infusion devices rely on very low flow rates of 0.5 cc to 4.0 cc per hour, and localized pooling of the medication can occur, leaving other portions of the wound untouched by the pain medication.

Based on the foregoing, integrated percutaneous infusion and aspiration system 35 takes advantage of the presence of a relative negative pressure source, or vacuum, provided within aspiration catheter 15. The negative pressure created by aspiration catheter is used in the present invention to control the flow of the infusion solution as it egresses from infusion catheter 10 so as to cause the infusion solution to perfuse the entire wound site as it travels toward aspiration catheter 15. The multitude of ports on both infusion catheter 10 and aspiration catheter 15 provide an array of opposing egress and ingress sites such that cross flow can be created between the two catheters to fully bathe the wound site with the infusion solution.

Furthermore, although not required, by integrating infusion catheter 10 with aspiration catheter 15, catheter assembly 20 can be efficiently and cleanly inserted into a single percutaneous tract to the wound. As a result, further incisions are not required and the potential for infection is minimized.

Furthermore, as discussed above, to achieve the desired flow of the infusion solution across the wound and the desired residency time of the infusion solution, a coordinated operation of the infusion and aspiration catheters has been developed. The flow rate within the aspiration and infusion catheters are controlled and synchronized to ensure that the infusion solution is not evacuated too quickly and to further ensure that the flow in the aspiration catheter is uninterrupted in order to minimize the potential for clot formations within the aspiration catheter that might otherwise clog the aspiration catheter.

Figure 3:
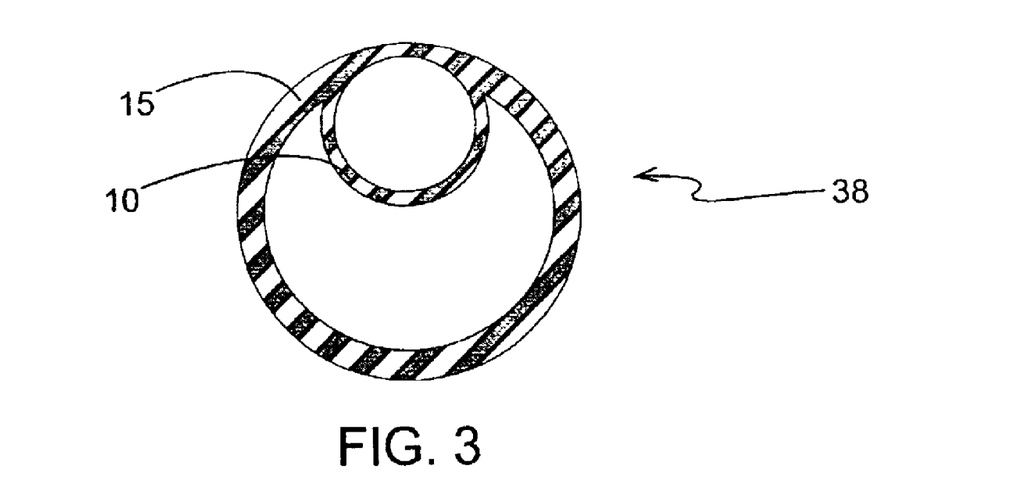
FIG. 3 is a cross section side view of an alternative embodiment of the catheter assembly shown in FIG. 2.

Flow control system 19 can be connected to a number of different embodiments of catheter assembly 20. Alternate embodiments of catheter assembly 20 are shown in FIGS. 3–9 with like elements being identified by like reference characters. For example, depicted in FIG. 3 is a transverse cross sectional view of a catheter assembly 38. As discussed above with regard to FIG. 2, in catheter assembly 20 infusion catheter 10 and aspiration catheter 15 are discrete catheters where, for a portion of the length, infusion catheter 10 resides within aspiration catheter 15. In contrast, although at least a portion of infusion catheter 10 resides within aspiration catheter 15 in catheter assembly 38, infusion catheter 10 and aspiration catheter 15 are integrally formed as a single unit, i.e., they share a common sidewall. In this embodiment, either a separate catheter or a separate portion of catheters 10 and 15 is used to connect one and/or both of the integrally formed catheters to flow control system 19.

Figure 4:
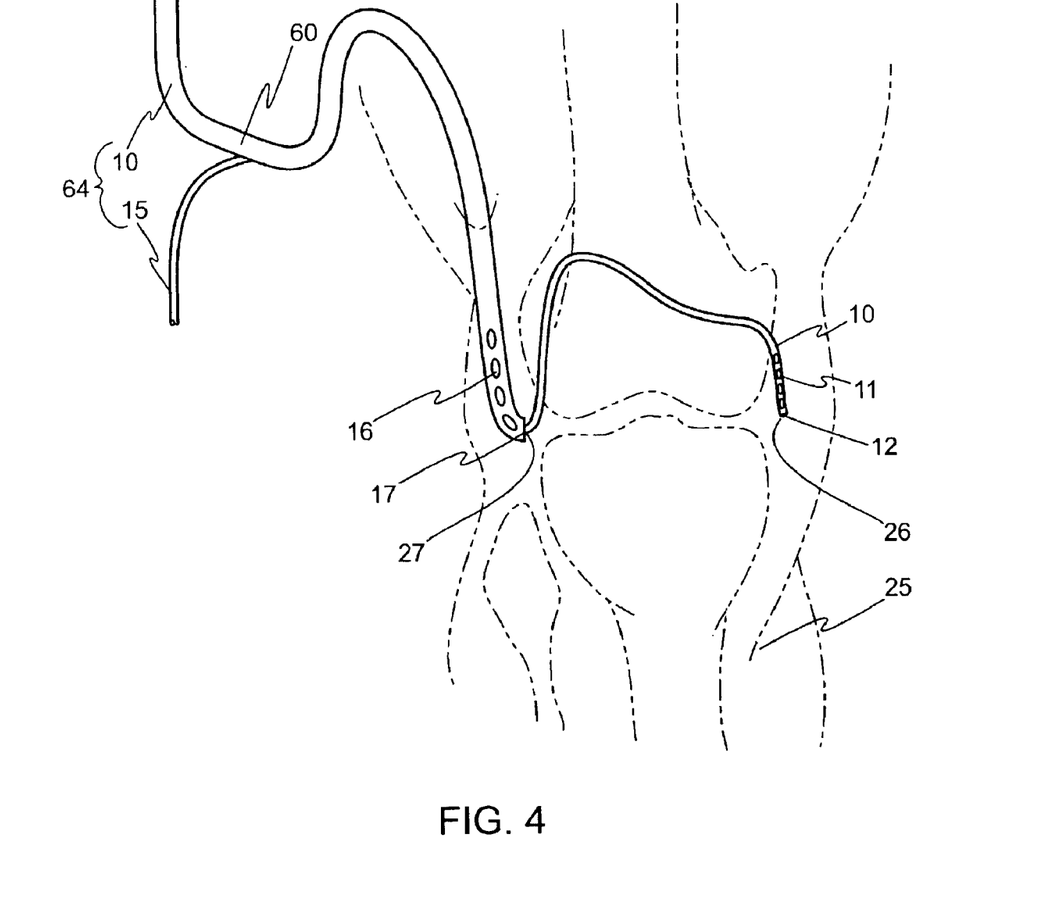
FIG. 4 is a schematic view of an alternative embodiment of the catheter assembly of the integrated infusion and aspiration system shown in FIG. 1.

Depicted in FIG. 4 is an alternative catheter assembly 64 where aspiration catheter 15 has an outside diameter smaller than the outside diameter of infusion catheter 10. In this embodiment, aspiration catheter 15 passes through the sidewall of infusion catheter 10 at proximal junction 60 so as to be disposed within first lumen 46 of infusion catheter 10. Aspiration catheter 15 extends distally within infusion catheter 10 and exits through end port 27 at distal end tip 17. Aspiration catheter 15 then continues to project beyond distal end tip 17 of infusion catheter 10. As with FIGS. 2 and 3, the coaxial portion of catheter assembly 64 can either comprise two discrete catheters or a single integrally formed catheter.

Figure 5:
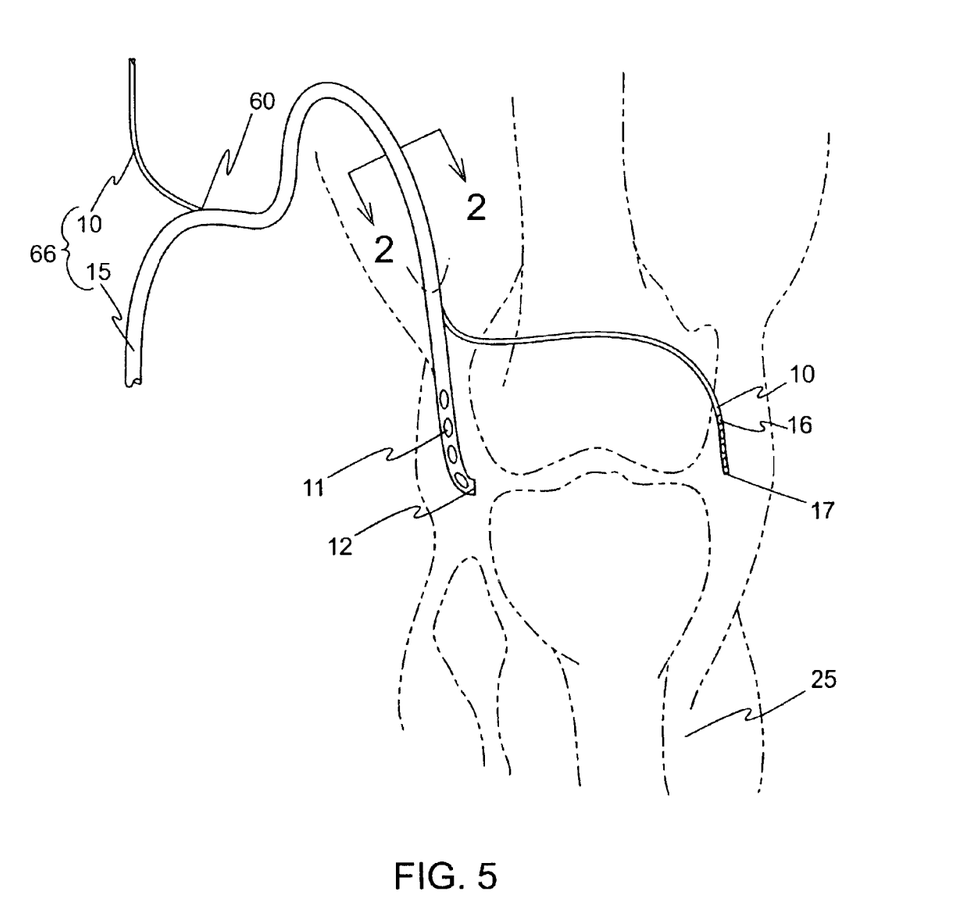
FIG. 5 is a schematic view of another alternative embodiment of the catheter assembly of the integrated infusion and aspiration system shown in FIG. 1.

FIG. 5 shows a catheter assembly 66 similar to catheter assembly 20 shown in FIG. 1. In contrast to infusion catheter 10 exiting aspiration catheter 15 at distal end tip 12, however, infusion catheter 10 exits aspiration catheter 15 by passing through the sidewall thereof proximal of distal end tip 12. As a result catheter assembly 66 is bifurcated at both opposing ends. Although the bifurcated distal end of infusion catheter 10 is shown as being longer than the free distal end of aspiration catheter 15, in alternative embodiments the bifurcated distal ends can be the same length or the distal end of aspiration catheter 15 can be longer.

Figure 6:
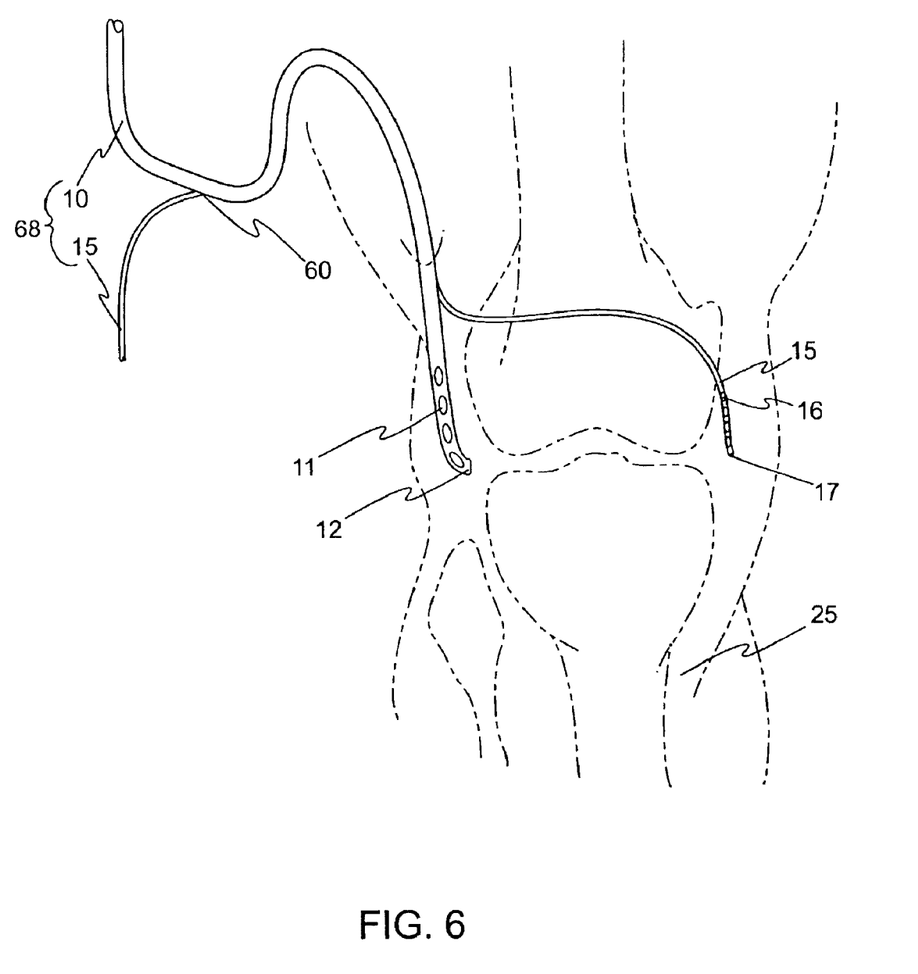
FIG. 6 is a schematic view of still another alternative embodiment of the catheter assembly of the integrated infusion and aspiration system shown in FIG. 1.

FIG. 6 shows a catheter assembly 68 similar to catheter assembly 64 shown in FIG. 4. Like catheter assembly 66 shown in FIG. 5, however, aspiration catheter 15 exits infusion catheter 10 by passing through the sidewall thereof proximal of distal end tip 12. Accordingly, catheter assembly 68 is also bifurcated at both opposing ends.

Figure 7:
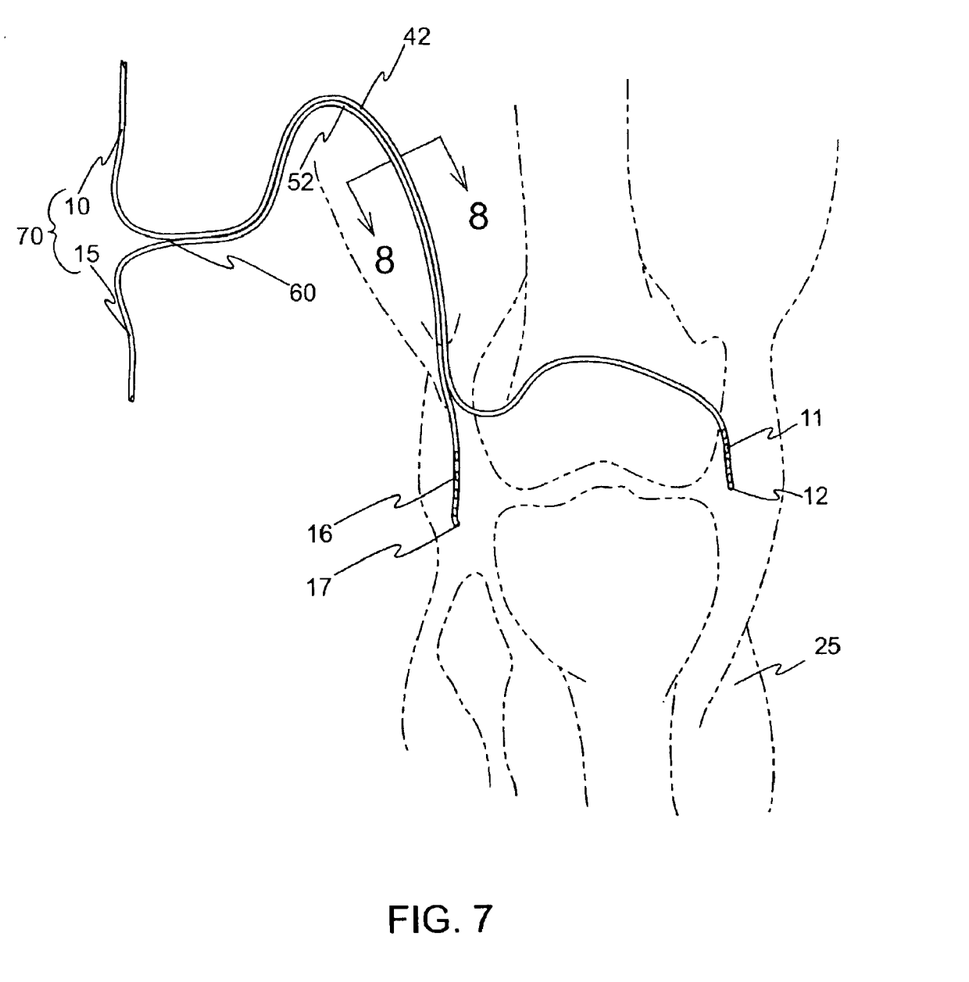
FIG. 7 is a schematic view of yet another alternative embodiment of the catheter assembly of the integrated infusion and aspiration system shown in FIG. 1.
Figure 8:
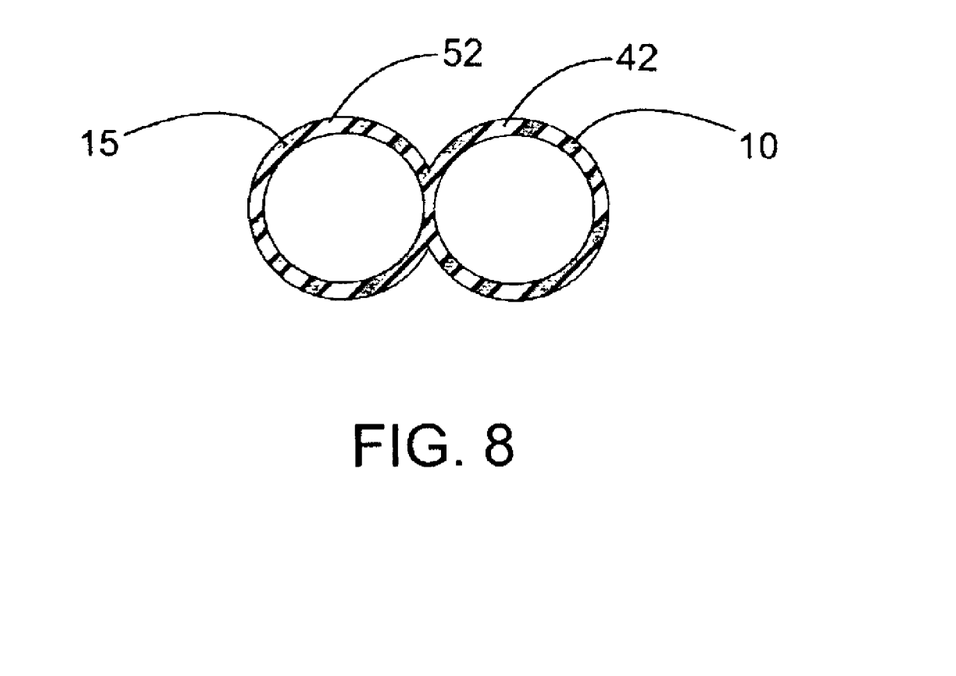
FIG. 8 is a cross sectional side view of the catheter assembly shown in FIG. 6 taken along section lines 8—8.

FIG. 7 shows a catheter assembly 70 wherein a least a portion of middle sections 42 and 52 of infusion catheter 10 and aspiration catheter 15, respectively, are integrally joined in a side-by-side arrangement. The opposing ends of catheter assembly 70 have been bifurcated. Depicted in FIG. 8 is a transverse cross sectional side view of one embodiment of the side-by-side arrangement. This integral connection between catheters 10 and 15 enables catheter assembly 70 to be inserted through a single incision in the skin.

Figure 9:
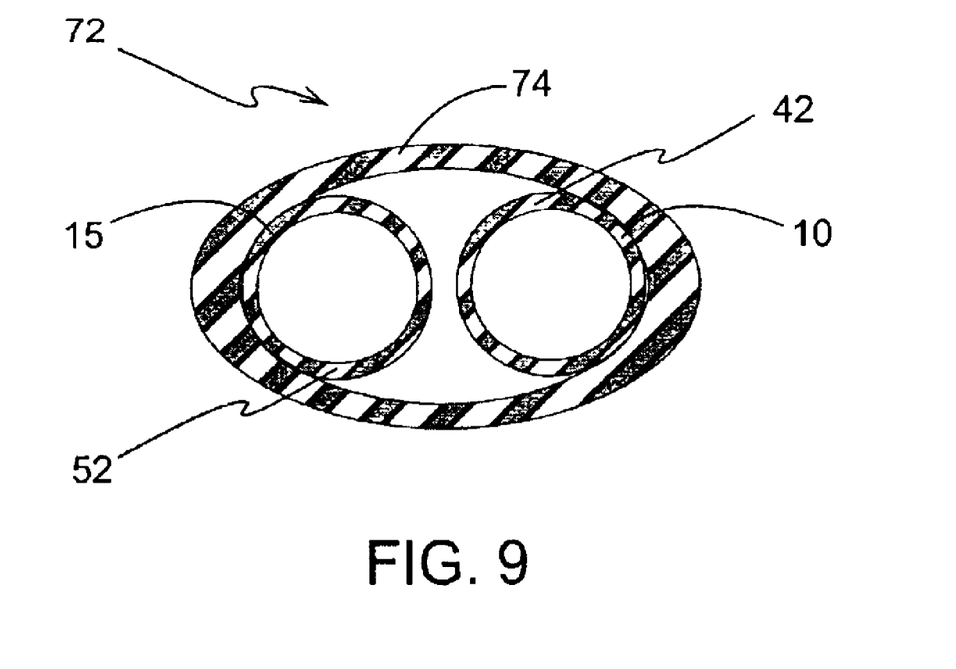
FIG. 9 is a cross sectional side view of an alternative embodiment of the catheter assembly shown in FIG. 8.

Finally, depicted in FIG. 9 is a catheter assembly 72 which comprises two discrete catheters 10 and 15. At least a portion of the middle sections 42 and 52 of catheters 10 and 15, respectively, are held together by an encircling outer tube 74. Outer tube 74 can be replaced by a wrap or a variety of other forms of connectors.

The present invention may be embodied in other specific forms without departing from its spirit or essential characteristics. Thus the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for percutaneous infusion and aspiration of an internal wound site, the system comprising:
   a catheter assembly comprising:
      an aspiration catheter having a proximal section and an opposing distal section, the aspiration catheter bounding a first lumen extending along the length thereof, at least one port being formed on the distal section of the aspiration catheter so as to communicate with the first lumen; and
      an infusion catheter having a proximal section and an opposing distal section, the infusion catheter bounding a second lumen extending along the length thereof at least one port being formed on the distal section of the infusion catheter so as to communicate with the second lumen, at least a portion of the aspiration catheter or infusion catheter being disposed within the lumen of the other of the aspiration catheter or infusion catheter, the distal section of the aspiration catheter and the distal section of the infusion catheter being spaced apart from each other so as not to be disposed within the lumen of the other;
   a medication reservoir in fluid communication with the proximal section of the infusion catheter;
   a first pump adapted to transfer fluid from the medication reservoir to the infusion catheter;
   an aspiration reservoir in fluid communication with the proximal section of the aspiration catheter;
   a second pump adapted to draw fluid from the aspiration catheter to the aspiration reservoir; and
   an electronic controller which selectively controls both the flow rate of the fluid through the infusion catheter and the flow rate of fluid through the aspiration catheter.

2. The system of claim 1 wherein the aspiration catheter comprises a distal end tip, the at least one port being formed on the distal end tip or proximal thereof.

3. The system of claim 1 further comprising a plurality of spaced apart ports formed on the corresponding distal sections of the infusion catheter and the aspiration catheter.

4. The system of claim 1 wherein the plurality of ports of the infusion catheter and the aspiration catheter each have a predetermined number and a predetermined spacing, the number and spacing of the plurality of ports on the infusion catheter being substantially the same as the number and spacing of plurality of ports on the aspiration catheter.

5. The system of claim 1 wherein the infusion catheter and the aspiration catheter are discrete members.

6. The system of claim 1 wherein at least a portion of the infusion catheter and the aspiration catheter are integrally formed as a one piece member.

7. The system of claim 1 wherein at least a portion of the infusion catheter is disposed within the first lumen of the aspiration catheter, the infusion catheter also either projecting out of the first lumen through a distal end tip of the aspiration catheter or through the aspiration catheter at a location proximal of the distal end tip.

8. The system of claim 1 wherein at least a portion of the aspiration catheter is disposed within the second lumen of the infusion catheter, the aspiration catheter also either projecting out of the second lumen through a distal end tip of the infusion catheter or through the infusion catheter at a location proximal of the distal end tip.

9. The system of claim 1 further comprising an infusion solution stored in the medication reservoir such that selectively activating the pumps causes the infusion solution to flow from the infusion catheter port to the aspiration catheter port such that the infusion solution is substantially evenly dispersed of over the wound site.

10. The system of claim 1 further comprising a first flow control apparatus disposed on the proximal section of the infusion catheter or between the medication reservoir and the proximal section of the infusion catheter.

11. The system of claim 1 further comprising a second flow control apparatus disposed on the proximal section of the aspiration catheter or between the aspiration reservoir and the proximal section of the aspiration catheter.

12. The system of claim 1 further comprising at least one power source adapted to activate the first pump and the second pump.

13. The system of claim 1 wherein the at least one port of the infusion catheter is spaced apart from the at least one port of the aspiration catheter by a distance of at least ten times the larger of a maximum outside diameter of the aspiration catheter or the infusion catheter.

14. The system of claim 1 wherein at least one of the first pump and the second pump comprises an electronic pump.

15. The system of claim 14 wherein the at least one of the first pump and the second pump is electrically coupled with the electronic controller.

16. The system of claim 1 further comprising a plurality of longitudinally spaced apart ports formed along the distal section of the aspiration catheter and a plurality of longitudinally spaced apart ports formed along the distal section of the infusion catheter, the distal section of the aspiration catheter and the distal section of the infusion catheter each being selectively positionable into a relaxed, linear configuration.

17. The system of claim 9 wherein the infusion solution comprises a medication selected from the group consisting of an antibiotic, an anti-inflammatory, an anesthetic, an analgesic, an antiseptic, an anticoagulant, and combinations thereof.

18. The system of claim 17 wherein the medication is an anesthetic selected from the group consisting of lidocaine, bupivacaine, ropivicaine, and combinations thereof.

19. A system for percutaneous infusion and aspiration of an internal wound site, the system comprising:
   a catheter assembly comprising:
      an aspiration catheter having a proximal section, a distal section, and a middle section extending therebetween, the aspiration catheter bounding a first lumen extending along the length thereof, a plurality of spaced apart ports extending through the distal section of the aspiration catheter so as to communicate with the first lumen; and
      an infusion catheter having a proximal section, a distal section, and a middle section extending therebetween, the infusion catheter bounding a second lumen extending along the length thereof, a plurality of spaced apart ports extending through the distal section of the infusion catheter so as to communicate with the second lumen, at least a portion of the middle section of the aspiration catheter or infusion catheter being disposed within the lumen of or being secured adjacent to the middle section of the other of the aspiration catheter or infusion catheter, the distal section of the aspiration catheter and the distal section of the infusion catheter each being selectively positionable into a relaxed, linear configuration, the distal section of the aspiration catheter and the distal section of the infusion catheter being spaced apart from each other so as not to be disposed within the lumen of the other;
   a medication reservoir in fluid communication with the proximal section of the infusion catheter;
   a first pump adapted to transfer fluid from the medication reservoir to the infusion catheter;
   an aspiration reservoir in fluid communication with the proximal section of the aspiration catheter; and
   a second pump adapted to draw fluid from the aspiration catheter to the aspiration reservoir.

20. The system of claim 19 wherein the plurality of ports of the infusion catheter and the aspiration catheter each have a predetermined number and a predetermined spacing, the number and spacing of the plurality of ports on the infusion catheter being substantially the same as the number and spacing of plurality of ports on the aspiration catheter.

21. The system of claim 19 wherein the infusion catheter and the aspiration catheter are discrete members.

22. The system of claim 19 wherein at least a portion of the infusion catheter and the aspiration catheter are integrally formed as a one piece member.

23. The system of claim 19 wherein at least a portion of the infusion catheter is disposed within the first lumen of the aspiration catheter, the infusion catheter also either projecting out of the first lumen through a distal end tip of the aspiration catheter or through the aspiration catheter at a location proximal of the distal end tip.

24. The system of claim 19 wherein at least a portion of the aspiration catheter is disposed within the second lumen of the infusion catheter, the aspiration catheter also either projecting out of the second lumen through a distal end tip of the infusion catheter or through the infusion catheter at a location proximal of the distal end tip.

25. The system of claim 19 further comprising an infusion solution stored in the medication reservoir such that selectively activating the pumps causes the infusion solution to flow from the infusion catheter ports to the aspiration catheter ports such that the infusion solution is substantially evenly dispersed of over the wound site.

26. The system of claim 19 further comprising a first flow control apparatus disposed on the proximal section of the infusion catheter or between the medication reservoir and the proximal section of the infusion catheter.

27. The system of claim 19 further comprising a second flow control apparatus disposed on the proximal section of the aspiration catheter or between the aspiration reservoir and the proximal section of the aspiration catheter.

28. The system of claim 19 further comprising at least one power source adapted to activate the first pump and the second pump.

29. The system of claim 19 wherein the plurality of ports on the infusion catheter are spaced apart from the plurality of ports on the aspiration catheter by a distance of at least ten time the larger of a maximum outside diameter of the aspiration catheter or the infusion catheter.

30. The system of claim 25 wherein the infusion solution comprises a medication selected from the group consisting of an antibiotic, an anti-inflammatory, an anesthetic, an analgesic, an antiseptic, an anticoagulant, and combinations thereof.

31. The system of claim 30 wherein the medication is an anesthetic selected from the group consisting of lidocaine, bupivacaine, ropivicaine, and combinations thereof.

32. A system for percutaneous infusion and aspiration of an internal wound site, the system comprising:

a catheter assembly comprising:

an aspiration catheter having a proximal section, an opposing elongated distal section having a terminal distal tip, and a central section disposed between the proximal section and the elongated distal section, the aspiration catheter bounding a first lumen extending along the length thereof, at least one port being formed on the elongated distal section of the aspiration catheter so as to communicate with the first lumen; and an infusion catheter having a proximal section, an opposing elongated distal section having a terminal distal tip, and a central section disposed between the proximal section and the elongated distal section, the infusion catheter bounding a second lumen extending along the length thereof, at least one port being formed on the distal section of the infusion catheter so as to communicate with the second lumen, at least a portion of the central section of the aspiration catheter and the infusion catheter being secured together or being disposed within the lumen of the other and the elongated distal section of the aspiration catheter and the elongated distal section of the infusion catheter being freely separated from each other so that no part of the infusion catheter is secured to or disposed within the elongated distal section of the aspiration catheter and no part of the aspiration catheter is secured to or disposed within the elongated distal section of the infusion catheter;

a medication reservoir in fluid communication with the proximal section of the infusion catheter;

a first pump adapted to transfer fluid from the medication reservoir to the infusion catheter;

an aspiration reservoir in fluid communication with the proximal section of the aspiration catheter; and a second pump adapted to draw fluid from the aspiration catheter to the aspiration reservoir.

33. The system of claim 32 further comprising a plurality of spaced apart ports formed on at least one of the elongated distal sections of the infusion catheter and the aspiration catheter.

34. The system of claim 32 further comprising an electronic controller which selectively controls both the flow rate of the fluid through the infusion catheter and the flow rate of fluid through the aspiration catheter.

* * * * *

UNITED STATES PATENT AND TRADEMARK OFFICE
CERTIFICATE OF CORRECTION

PATENT NO. : 6,893,414 B2
DATED : May 17, 2005
INVENTOR(S) : E. Marlowe Goble et al.

It is certified that error appears in the above-identified patent and that said Letters Patent is hereby corrected as shown below:

Title page,
Item [56], References Cited, U.S. PATENT DOCUMENTS,
change "Gloukhoff, et al." to -- Work, et al. --.
Item [57], ABSTRACT,
Line 1, after "system includes" remove "of".
Line 9, change "provides" to -- provide --.

Column 3,
Line 14, after "conventional" insert -- forms. --.

Column 5,
Line 6, after "based" insert -- on --.
Line 67, change "catheter 10" to -- catheter 15 --.

Column 6,
Line 25, change "period time" to -- time period --.

Signed and Sealed this

Seventeenth Day of January, 2006

JON W. DUDAS
*Director of the United States Patent and Trademark Office*